US008916375B2

(12) United States Patent
Landers et al.

(10) Patent No.: US 8,916,375 B2
(45) Date of Patent: Dec. 23, 2014

(54) INTEGRATED MICROFLUIDIC ANALYSIS SYSTEMS

(75) Inventors: James P. Landers, Charlottesville, VA (US); Joan Marie Bienvenue, Fredericksburg, VA (US); Lindsay Ann Legendre, Charlottesville, VA (US); Christopher J. Easley, Auburn, AL (US); James M. Karlinsey, Audubon, PA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1777 days.

(21) Appl. No.: 12/090,233

(22) PCT Filed: Oct. 12, 2006

(86) PCT No.: PCT/US2006/039809
§ 371 (c)(1),
(2), (4) Date: Dec. 22, 2008

(87) PCT Pub. No.: WO2007/047336
PCT Pub. Date: Apr. 26, 2007

(65) Prior Publication Data
US 2009/0170092 A1    Jul. 2, 2009

Related U.S. Application Data

(60) Provisional application No. 60/726,027, filed on Oct. 12, 2005.

(51) Int. Cl.
| | |
|---|---|
| *C12M 1/36* | (2006.01) |
| *C12M 1/38* | (2006.01) |
| *C12M 3/00* | (2006.01) |
| *C12Q 1/68* | (2006.01) |
| *B01D 57/02* | (2006.01) |

(52) U.S. Cl.
USPC .................. 435/286.5; 435/6.12; 204/451

(58) Field of Classification Search
USPC ............... 435/6, 6.12, 283.1, 286.5; 204/451
See application file for complete search history.

(56) References Cited

U.S. PATENT DOCUMENTS

| | | |
|---|---|---|
| 5,849,208 A | 12/1998 | Hayes et al. |
| 5,958,349 A | 9/1999 | Petersen et al. |

(Continued)

FOREIGN PATENT DOCUMENTS

| | | |
|---|---|---|
| WO | WO-2006039293 A1 | 4/2006 |
| WO | WO-2006093865 A1 | 9/2006 |
| WO | WO-2007047336 A3 | 4/2007 |

OTHER PUBLICATIONS

"International Application Serial No. PCT/US2006/039809, International Preliminary Report on Patentability mailed Apr. 16, 2008", 4 pgs.

(Continued)

*Primary Examiner* — Robert T. Crow
(74) *Attorney, Agent, or Firm* — Schwegman Lundberg & Woessner, P.A.

(57) ABSTRACT

The present invention provides an integrated microfluidic analysis system. The system contains at least a first (pre-reaction treatment) domain for treating a sample prior to subjecting the sample to a chemical reaction. The following domains are optionally added to the first domain: a second (reaction) domain for reacting the chemical of interest in the sample; and a third (post-reaction separation) domain for separating products and reactants coming out of the reaction domain. The integrated microfluidic analysis system of the present invention is most applicable to PCR analysis.

24 Claims, 10 Drawing Sheets

(56) References Cited

U.S. PATENT DOCUMENTS

| | | | |
|---|---|---|---|
| 6,312,929 B1 | 11/2001 | McMillan | |
| 6,368,871 B1 | 4/2002 | Christel et al. | |
| 6,369,893 B1 | 4/2002 | Christel et al. | |
| 6,374,684 B1 | 4/2002 | Dority | |
| 6,403,037 B1 | 6/2002 | Chang et al. | |
| 6,431,476 B1 | 8/2002 | Taylor et al. | |
| 6,432,290 B1 | 8/2002 | Harrison et al. | |
| 6,440,725 B1 | 8/2002 | Pourahmadi et al. | |
| 6,517,234 B1 | 2/2003 | Kopf-Sill et al. | |
| 6,534,645 B2 | 3/2003 | McMillian | |
| 6,551,841 B1 * | 4/2003 | Wilding et al. | 436/518 |
| 6,565,815 B1 | 5/2003 | Chang et al. | |
| 6,620,625 B2 | 9/2003 | Wolk et al. | |
| 6,630,353 B1 | 10/2003 | Parce et al. | |
| 6,660,228 B1 | 12/2003 | Chang et al. | |
| 6,664,104 B2 | 12/2003 | Pourahmadi et al. | |
| 6,692,700 B2 | 2/2004 | Handique | |
| 6,713,297 B2 | 3/2004 | McMillan et al. | |
| 6,739,531 B2 | 5/2004 | Taylor | |
| 6,783,736 B1 | 8/2004 | Taylor et al. | |
| 6,783,934 B1 | 8/2004 | McMillan et al. | |
| 6,818,185 B1 | 11/2004 | Petersen et al. | |
| 6,819,027 B2 | 11/2004 | Saraf | |
| 6,878,540 B2 | 4/2005 | Pourahmadi et al. | |
| 6,881,541 B2 | 4/2005 | Petersen et al. | |
| 6,887,693 B2 | 5/2005 | Mcmillan et al. | |
| 6,893,879 B2 | 5/2005 | Petersen et al. | |
| 6,911,327 B2 | 6/2005 | Mcmillan et al. | |
| 6,914,137 B2 | 7/2005 | Baker | |
| 6,919,046 B2 | 7/2005 | O'Connor et al. | |
| 6,931,292 B1 | 8/2005 | Brumitt et al. | |
| 6,940,598 B2 | 9/2005 | Christel et al. | |
| 6,942,971 B2 | 9/2005 | McMillan et al. | |
| 6,979,424 B2 | 12/2005 | Northrup et al. | |
| 6,987,018 B2 | 1/2006 | Taylor et al. | |
| 7,101,509 B2 | 9/2006 | Chang et al. | |
| 7,135,144 B2 | 11/2006 | Christel et al. | |
| 7,188,001 B2 | 3/2007 | Young et al. | |
| 7,226,732 B2 | 6/2007 | Sakai et al. | |
| 7,255,833 B2 | 8/2007 | Chang et al. | |
| 7,294,466 B2 | 11/2007 | McMillan | |
| 7,410,760 B2 | 8/2008 | Swenson | |
| 7,462,323 B1 | 12/2008 | Chang et al. | |
| 7,569,346 B2 | 8/2009 | Petersen et al. | |
| 7,575,721 B2 | 8/2009 | Chang et al. | |
| 7,621,418 B2 | 11/2009 | Chang | |
| 7,687,232 B2 | 3/2010 | Gyllensten et al. | |
| 7,803,549 B2 | 9/2010 | Swenson | |
| 7,914,994 B2 | 3/2011 | Petersen | |
| 2001/0012612 A1 | 8/2001 | Petersen et al. | |
| 2001/0019114 A1 | 9/2001 | Arakawa et al. | |
| 2002/0019060 A1 | 2/2002 | Petersen et al. | |
| 2002/0025576 A1 | 2/2002 | Northrup et al. | |
| 2002/0031768 A1 | 3/2002 | McMillan et al. | |
| 2002/0034745 A1 | 3/2002 | McMillan et al. | |
| 2002/0034746 A1 | 3/2002 | McMillan et al. | |
| 2002/0039783 A1 | 4/2002 | McMillan et al. | |
| 2002/0042125 A1 | 4/2002 | Petersen et al. | |
| 2002/0045246 A1 | 4/2002 | McMillan et al. | |
| 2002/0055167 A1 | 5/2002 | Pourahmadi et al. | |
| 2002/0058282 A1 | 5/2002 | McMillan | |
| 2002/0109844 A1 | 8/2002 | Christel et al. | |
| 2002/0168299 A1 | 11/2002 | Chang et al. | |
| 2002/0175079 A1 | 11/2002 | Christel et al. | |
| 2002/0187547 A1 | 12/2002 | Taylor et al. | |
| 2003/0017467 A1 * | 1/2003 | Hooper et al. | 435/6 |
| 2003/0066915 A1 | 4/2003 | Taylor | |
| 2003/0152492 A1 | 8/2003 | Chang et al. | |
| 2003/0162304 A1 | 8/2003 | Dority et al. | |
| 2003/0164658 A1 | 9/2003 | Saraf | |
| 2003/0221771 A1 | 12/2003 | Chang et al. | |
| 2004/0086872 A1 | 5/2004 | Childers et al. | |
| 2004/0096819 A1 | 5/2004 | McMillan | |
| 2004/0101859 A1 | 5/2004 | Moon | |
| 2004/0122559 A1 | 6/2004 | Young et al. | |
| 2004/0126796 A1 * | 7/2004 | Carlson et al. | 435/6 |
| 2004/0166031 A1 | 8/2004 | Taylor et al. | |
| 2004/0200909 A1 | 10/2004 | McMillan et al. | |
| 2004/0209354 A1 | 10/2004 | Mathies et al. | |
| 2005/0003374 A1 | 1/2005 | Swenson | |
| 2005/0042137 A1 | 2/2005 | Petersen et al. | |
| 2005/0069898 A1 | 3/2005 | Moon et al. | |
| 2005/0095603 A1 | 5/2005 | Mokkapati et al. | |
| 2005/0194316 A1 | 9/2005 | Pourahmadi et al. | |
| 2005/0244837 A1 | 11/2005 | McMillan et al. | |
| 2005/0255516 A1 | 11/2005 | McMillan et al. | |
| 2006/0014200 A1 | 1/2006 | McMillan | |
| 2006/0019379 A1 | 1/2006 | Taylor et al. | |
| 2006/0027686 A1 | 2/2006 | Taylor et al. | |
| 2006/0068398 A1 | 3/2006 | McMillan | |
| 2006/0068399 A1 | 3/2006 | McMillan et al. | |
| 2006/0073484 A1 | 4/2006 | Mathies et al. | |
| 2006/0169708 A1 | 8/2006 | Chang | |
| 2006/0177844 A1 | 8/2006 | Ching et al. | |
| 2006/0229441 A1 | 10/2006 | Gall | |
| 2006/0275178 A1 | 12/2006 | Chang et al. | |
| 2007/0259362 A1 | 11/2007 | Sakai et al. | |
| 2008/0014114 A1 | 1/2008 | Van Atta et al. | |
| 2008/0038737 A1 | 2/2008 | Smith et al. | |
| 2008/0057572 A1 | 3/2008 | Petersen et al. | |
| 2008/0193946 A1 | 8/2008 | Mcmillan | |
| 2008/0227090 A1 | 9/2008 | Sakai et al. | |
| 2008/0254532 A1 | 10/2008 | Chang et al. | |
| 2008/0286151 A1 | 11/2008 | Chang et al. | |
| 2008/0286798 A1 | 11/2008 | Swenson | |
| 2009/0047669 A1 | 2/2009 | Zhang et al. | |
| 2009/0062135 A1 | 3/2009 | Delfour et al. | |
| 2009/0308886 A1 | 12/2009 | Chang et al. | |
| 2010/0068706 A1 | 3/2010 | Pourahmadi et al. | |
| 2010/0129827 A1 | 5/2010 | Mcmillan | |
| 2010/0136569 A1 | 6/2010 | Moon et al. | |
| 2010/0233704 A1 | 9/2010 | Michot et al. | |
| 2010/0240049 A1 | 9/2010 | Svanholm Barrie et al. | |
| 2011/0053155 A1 | 3/2011 | Gall | |

OTHER PUBLICATIONS

"International Application Serial No. PCT/US2006/039809, Written Opinion mailed Apr. 19, 2007", 3 pgs.

* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Bacillus anthracis

<400> SEQUENCE: 1
caaatcagct cgaaagttag ga                                              22

<210> SEQ ID NO 2
<211> LENGTH: 27
<212> TYPE: DNA
<213> ORGANISM: Bacillus anthracis

<400> SEQUENCE: 2
cagtaactgt tcagaaggta catctga                                         27
```

INTEGRATED MICROFLUIDIC ANALYSIS SYSTEMS

This application is a National Phase of PCT/US2006/039809, filed Oct. 12, 2006, which claims priority to provisional application No. 60/726,027, filed Oct. 12, 2005, both of which are all incorporated herein by reference.

BACKGROUND OF THE INVENTION

Many applications in the field of chemical and biological requires separation of chemical components prior to or after reacting the chemicals. Examples of reactions requiring separation of components include organic, inorganic, biochemical, and molecular reactions. Examples of chemical reactions include thermal cycling amplification, such as polymerase chain reaction (PCR), ligase chain reaction (LCR), isothermal nucleic acid amplification, self-sustained sequence replication, enzyme kinetic studies, homogeneous ligand binding assays, affinity binding assays, and more complex biochemical mechanistic studies. Conventional separation techniques include electrophoresis, such as capillary electrophoresis, synchronized cyclic electrophoresis, and free flow electrophoresis. Conventional separation techniques also include isoelectric focusing (IEF), hybridization, liquid and gas chromatography, molecular sieving and filtering.

Of increasing interest in the field of chemical separation is the use of devices that include an integrated reaction chamber and separation regions. Such integrated devices provide a number of advantages over conventional devices in which one transfers a fluid sample between a reaction apparatus and a separation device and/or vice versa. For example, where the chemical reaction and separation steps are performed in a single integrated device, one may avoid contamination and crossover of sample or reaction products. In addition, an integrated device may allow for substantially faster sample processing and analysis.

Recent efforts to integrate processing and analytical functionalities in a single device, especially in the field of MEMS, microfabrication, and microfluidics, have resulted in the development of devices that include multiple substrates bonded together. The substrates are usually bonded with adhesives, or by heat sealing, fusion bonding, or anodic bonding. These multi-substrate devices typically include a reaction chamber that is connected to a separate separation component, such as a capillary tube containing a suitable electrophoresis gel, by an adhesive such as epoxy. Alternatively, these multi-substrate devices have reaction chambers and separation channels etched into a plate and a cover bonded over the top of the plate. For example, U.S. Pat. No. 5,849,208 to Hayes et al. and U.S. Pat. No. 6,979,424 to Northrup et al. disclose such devices. However, these prior art devices do not address sample preparation prior to reacting the chemicals. This is a particular difficult problem because certain chemicals used in pre-reaction sample preparation may detrimentally affect the reaction itself.

One application of particular interest is the polymerase chain reaction (PCR). Since the technique was first described two decades ago, PCR has become an essential tool in the field of genetic analysis, providing an in vitro method to amplify DNA sequences of interest. However, while conventional techniques are improving in speed, they are still time consuming (1-3 h per amplification), and the reagents are expensive at the volumes needed for manual transfer of samples between pre-treatment, amplification, and analysis steps. Furthermore, the conventional method of PCR product analysis, gel electrophoresis, has similar limitations in time and reagent volumes.

An solution to these problems was proposed by Manz et al. (Sens. Actuators B, 1990, 1:244-248) in the form of miniaturized total chemical analysis systems (R-TAS), where microfabricated fluidic networks could be utilized for sampling, pre-treatment, and analysis/detection of samples as well as the transport between the different domains. The development of these integrated microfluidic systems for genetic analysis has been a major research focus since the systems were proposed, with particular motivation from the clinical and forensic sciences. However, after more than a decade and a half after Manz et al.'s proposal, no bona fide microfluidic device has been demonstrated that is capable of nanoliter flow control with comprehensive sample pretreatment integrated with an analytical step for genomic analysis of whole blood.

Therefore, there remains a need for a µ-TAS capable of pre-reaction sample treatment, reaction, and post-reaction chemical separation all on one chip; and methods of efficiently operating such µ-TAS to eliminate poisoning of the reaction by reactants used in the sample treatment.

SUMMARY OF THE INVENTION

The present invention provides an integrated microfluidic analysis system. The system contains at least a first (pre-reaction treatment) domain for treating a sample prior to subjecting the sample to a chemical reaction. The following domains may also be fluidly connected to the first domain: a second (reaction) domain for reacting the chemical of interest in the sample, and a third (post-reaction separation) domain for separating products and reactants coming out of the reaction domain.

"Fluidly connected" or variations thereof, as used herein, refers to a condition wherein two domains are connected to each other such that fluid can pass from one domain to another.

The term "microfluidic" as used herein refers to an apparatus for analysis of small volumes of sample, and containing microscale components for fluid processing, such as channels, pumps, micro-reaction chambers, electrophoresis modules, microchannels, fluid reservoirs, detectors, valves, or mixers. These microfluidic apparatuses are also referred to as micro-total analysis systems (µTAS). "Micro" as used herein refers to small components and is not restricted to micron or microliter scale, but also include smaller components in the nanometer or nanoliter range.

The pre-reaction treatment domain is used to separate, purify, and concentrate the reactant(s) prior to the subjecting the reactant(s) to a reaction. Preferably, this includes at least a solid phase extraction column, such as electrophoresis column, chromatography column, affinity binding column, or the like. The pre-reaction treatment domain selectively isolates the reactant(s) from a sample containing a mixture of components. For example, if the sample is a whole blood sample, the pre-reaction domain contains an extraction column for purifying nucleic acids from the sample.

The reaction domain contains a reaction chamber, fluidly connected to the pre-reaction domain, for reacting the reactant(s). Here, the purified reactant(s) from the pre-reaction treatment domain is flowed in to the reaction chamber. The reaction domain may also be fluidly connected to other reservoirs for receiving further reactants, chemicals, catalysts, buffers, etc. For example, if the reaction is a PCR, other reservoirs can provide enzymes, nucleotides, buffers, etc., or accept waste from the reaction domain.

The post-reaction separation domain is used to separate the products and/or reactants coming from the reaction domain. Preferably, this includes at least a separation apparatus, such as electrophoresis column, chromatography column, affinity column, or the like. For example, if the reaction is a PCR, the post-reaction separation domain is preferably a capillary electrophoresis to separate the amplification products.

The apparatus may contain a pre-reaction treatment domain alone; a pre-reaction treatment domain and a reaction domain; or all three domains together. When used together, the domains are fluidly connected, and preferably separated by valves.

BRIEF DESCRIPTION OF THE DRAWINGS

The foregoing background and summary, as well as the following detailed description of the preferred embodiment, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

DETAILED DESCRIPTION OF THE PREFERRED EMBODIMENT

The present invention relates to a fully integrated microfluidic analysis system. Microfluidic devices and analysis systems typically include micromachined fluid networks. Fluid samples and reagents are brought into the device through entry ports and transported through channels to a reaction chamber, such as a thermally controlled reactor where mixing and reactions (e.g., synthesis, labeling, energy-producing reactions, assays, separations, or biochemical reactions) occur. The biochemical products may then be moved, for example, to an analysis module, where data is collected by a detector and transmitted to a recording instrument. The fluidic and electronic components are preferably designed to be fully compatible in function and construction with the reactions and reagents.

There are many formats, materials, and size scales for constructing microfluidic devices. Common microfluidic devices are disclosed in U.S. Pat. No. 6,692,700 to Handique et al.; U.S. Pat. No. 6,919,046 to O'Connor et al.; U.S. Pat. No. 6,551,841 to Wilding et al.; U.S. Pat. No. 6,630,353 to Parce et al.; U.S. Pat. No. 6,620,625 to Wolk et al.; and U.S. Pat. No. 6,517,234 to Kopf-Sill et al.; which are incorporated herein by reference. Typically, a microfluidic device is made up of two or more substrates bonded together. Microscale components for processing fluids are disposed on a surface of one or more of the substrates. These microscale components include, but are not limited to, reaction chambers, electrophoresis modules, microchannels, fluid reservoirs, detectors, valves, or mixers. When the substrates are bonded together, the microscale components are enclosed and sandwiched between the substrates. In many embodiments, inlet and outlet ports are engineered into the device for introduction and removal of fluid from the system. The microscale components can be linked together to form a fluid network for chemical and/or biological analysis. Those skilled in the art will recognize that substrates composed of silicon, glass, ceramics, polymers, metals, and/or quartz are all acceptable in the context of the present invention. Further, the design and construction of the microfluidic network vary depending on the analysis being performed and are within the ability of those skilled in the art.

Figure 1:
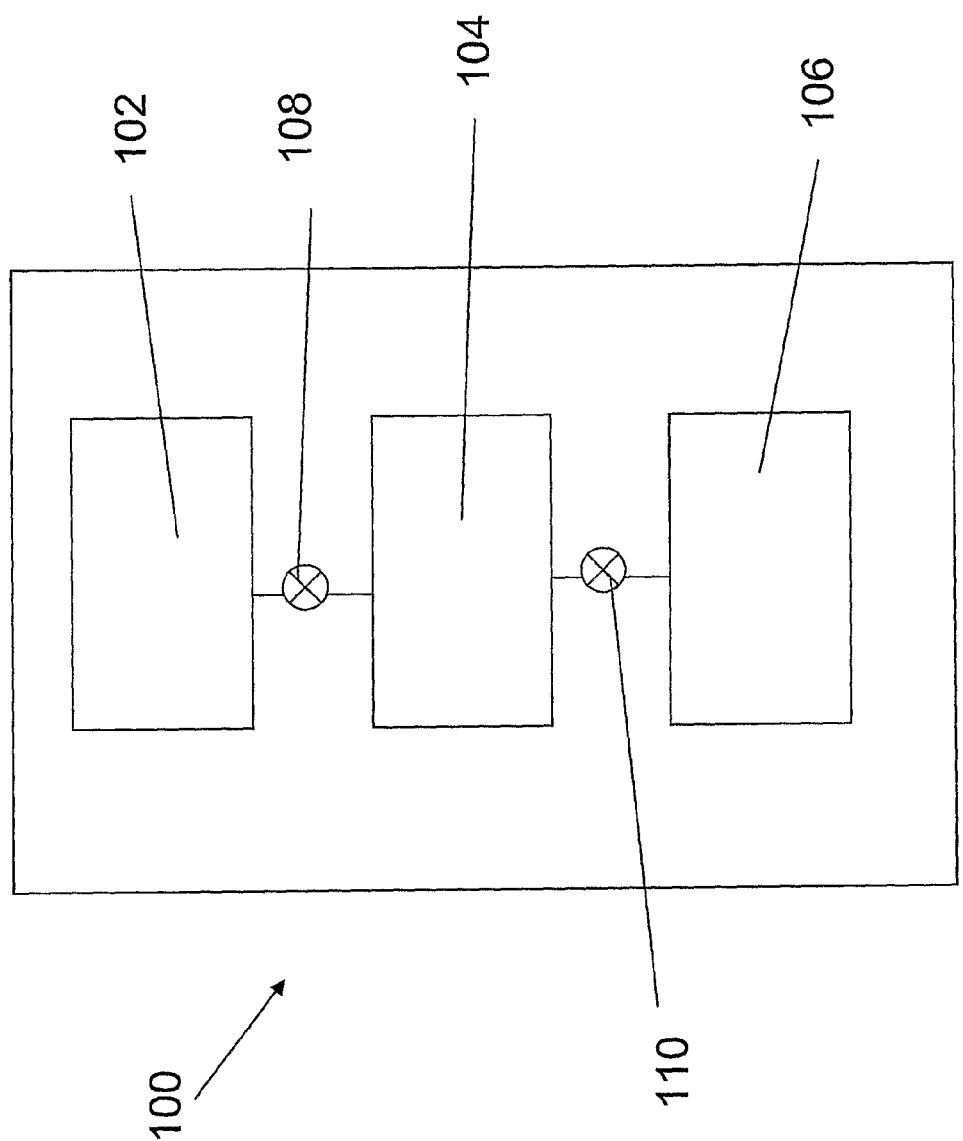
FIG. 1 is a schematic of the integrated microfluidic analysis system of the present invention.

Referring to FIG. 1, in a preferred embodiment, the system 100 of the present invention contains at least three fluidly connected domains: a first (pre-reaction treatment) domain 102 1 for treating a sample prior to subjecting the sample to a chemical reaction; a second (reaction) domain 104 for reacting the chemical of interest in the sample; and a third (post-reaction separation) domain 106 for separating products and reactants coming out of the reaction domain. In a preferred embodiment, the domains are separated from each other by valves, for example 108, 110.

The output of the pre-reaction treatment domain 102 feeds into the reaction domain 104; and the output of the reaction domain 104 feeds into the post reaction separation domain 106. Each of the domains may also contain input from other reservoirs and functional domains to effect its respective function. For example, the reaction domain may also accept inputs from various reservoirs to provide enzymes, nucleotides, buffers, etc., or to accept waste from the reaction domain. Each domain may also be surrounded by external, functional components such as electromotive sources, heaters, light sources, and optical detectors.

In use, a fluid sample is moved from one domain to another and the sample flow is controlled between domains. There may be more than one pre-reaction treatment domain, more than one reaction chamber, or more than one post reaction separation domain in a single integrated device of the present invention. However, at least one of the domains, most preferably the pre-reaction treatment domain, is required for the present invention.

Flow between the reaction chamber and the separation region may be by differential pressure, hydrodynamic forces, electrical motive forces, capillary action, pneumatic forces, hydraulic forces, mechanical forces, etc. The device may be coupled to instruments to actuate fluid flow such as pumps, vacuums, electrical connections, and the like. Electromotive mobility of molecules, and especially nucleic acids, as in isoelectric focus and electrophoretic mobility, is a convenient movement mechanism because of the predictability of movement. Preferably, however, pumping may be effected by the valves separating the domains.

Figure 2:
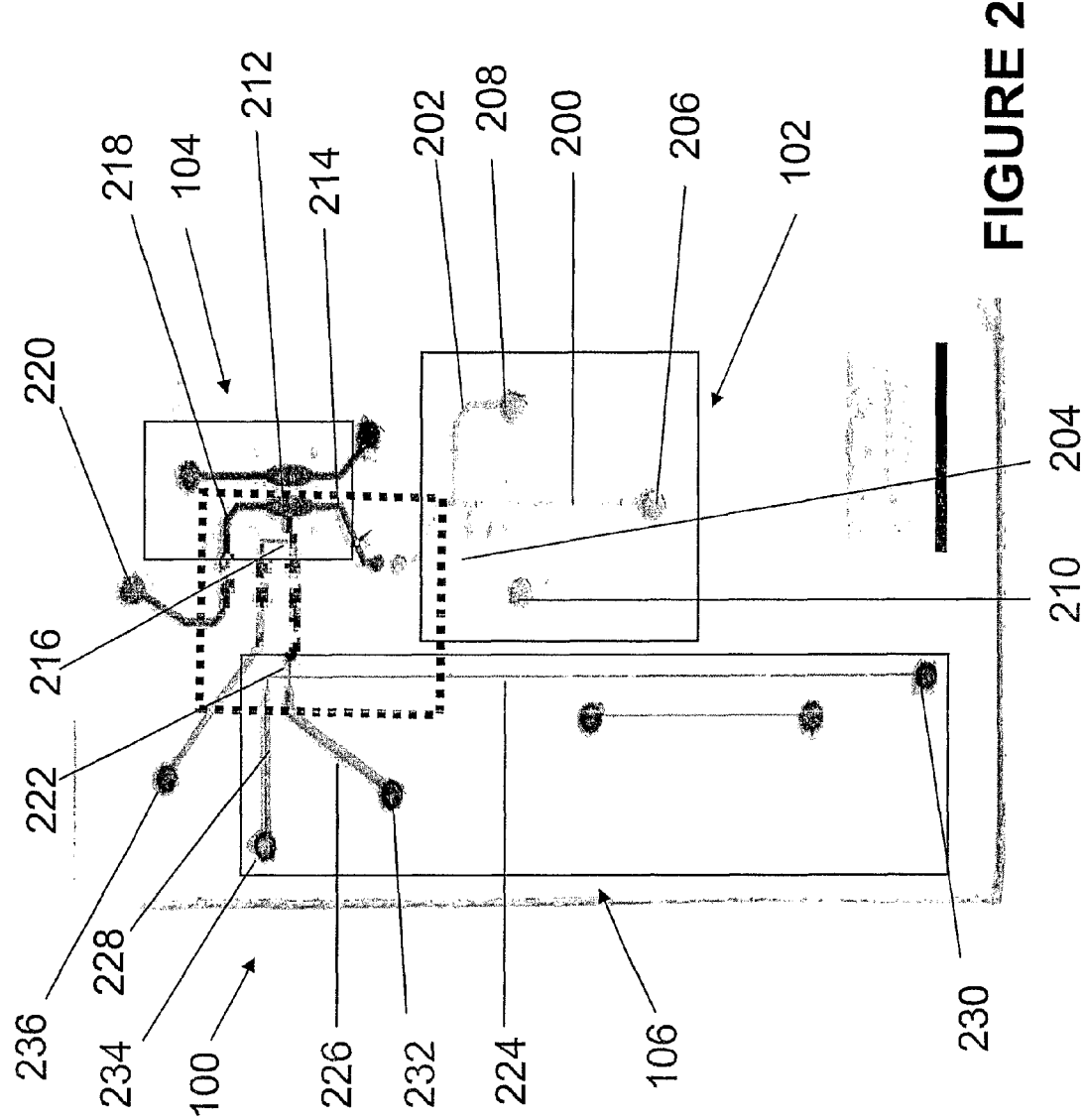
FIG. 2 is a drawing showing the preferred integrated microfluidic analysis system.
Figure 3:
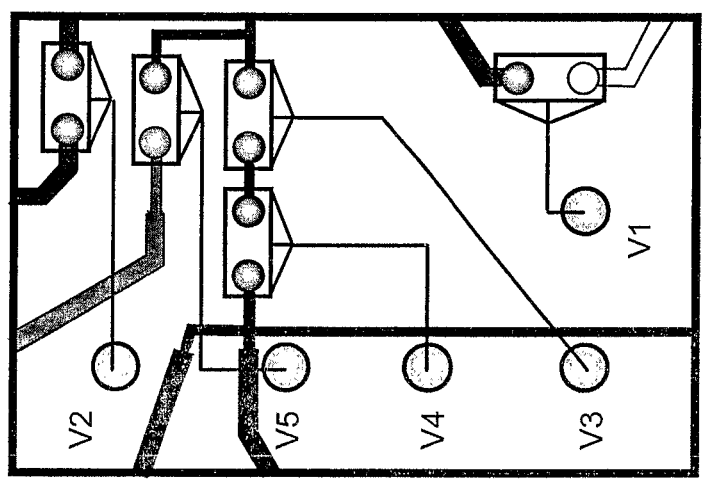
FIG. 3 is a drawing showing details of the valving system shown in the dashed box of FIG. 2.

FIG. 2 shows a preferred embodiment of the present invention where the integrated microfluidic analysis system 100 contains a pre-reaction treatment domain 102, a reaction domain 104, and a post-reaction separation domain 106. Although not required, these domains are separated by valves (inside the dashed box) that are shown in FIG. 3. The domains are connected through a network of channels and vias.

The pre-reaction treatment domain 102 contains a main channel 200, a side arm channel 202 and an exit arm channel 204, each of which contains reservoirs to collect and/or dispense fluid into the pre-reaction treatment domain. The main channel 200 has its corresponding sample inlet 206; the side arm channel 202 has its corresponding extraction reservoir 208; and the exit arm channel 204 has its corresponding exit arm reservoir 210. The exit arm channel 204 is preferably a high flow resistance microchannel, having a flow resistance higher than that of the main channel 200 and the side arm channel 202, preferably at least 2 times greater flow resistance, more preferably at least 10 times greater flow resistance, and most preferably 100 times greater flow resistance. Increased flow resistance can be accomplish by having a smaller cross-sectional area of the channel, a longer channel length, or a combination of both, because flow resistance is proportional to the channel length and inversely proportional to the cross-sectional area of the channel. In a preferred embodiment, to increase the flow resistance, the length of the exit arm channel 204 can be increased using switchbacks as illustrated in FIG. 2. The exit arm channel 204 and the side arm channel 202 intersect the main channel 200 along its length. In a preferred embodiment, the exit arm channel 204 is upstream of the side arm channel 202 to prevent contact of extraction solvents with any valve separating the pre-reaction treatment domain 102 and the reaction domain 104.

The main channel 200 is preferably packed with materials to selectively purifying the analyte (reactant for the reaction) to be subjected to a reaction in the reaction domain 104. The materials may contain binding sites capable of reversibly binding the analyte to enable the selective isolation of the analyte from a sample. The materials may be antibodies, oligonucleotides, enzymes, silica, charge switching materials, chitosan sol-gel, etc. For the purification of nucleic acids, the preferred materials is chitosan sol-gel, as disclosed in WO 2006/093865 to Wen et al., which is incorporated herein by reference.

The reaction domain 104 contains a reaction main inlet channel 214, a reaction chamber 212, and a reaction exit channel 216. In certain embodiments, a storage reservoir 220 can be used to store excess reactant(s) from the reaction chamber 212. This storage reservoir 220 is preferably separated from the reaction chamber 212 by valve V2. Additionally, it may be desirable to add materials, such as molecular weight markers, dyes, etc., to the reaction product before separation. In this case, the reaction exit channel 216 may also be connected to an addition reservoir 236 to effect addition of such materials.

The post-reaction separation domain 106 contains a separation inlet channel 222, a main separation channel 224, a buffer inlet channel 228, and a separation waste channel 226. At the end of the main separation channel 224 is a buffer waste reservoir 230. The buffer inlet channel 228 receives buffer solution from a buffer reservoir 234. The separation waste channel 226 expunges waste into the separation waste reservoir 232. Because it is desirable to control injection into the main separation channel 224, it is preferred that the main separation channel 224 has a higher flow resistance than the separation waste channel 226. As such, most of the reaction product will flow into the separation waste channel 224 and only a small plug will flow into the main separation channel 224. In certain embodiments, this improves the separation efficiency, particularly when electrophoresis is used.

Over all, the three domains are fluidly connected to each other as follows: the main channel 200 connects to the reaction main inlet channel 214, and the reaction exit channel 216 connects to the main separation channel 224.

Preferably, a valving system is used to control fluid flow in the integrated microfluidic system. The valves can be any known microvalves known in the art, such as an on-off valve, a pinch-off valve, a membrane valve, or the like, to prevent fluid from flowing through the valve when in a closed position and to permit fluid flow when in an open position. However, the preferred valves are diaphragm valves, such as those disclosed in U.S. Patent Publication No. 2004/0209354 to Mathies et al., which is incorporated herein by reference.

A preferred valving system is shown in FIG. 2 (dashed box) and in further detail in FIG. 3. The valves are shown as open rectangles: V1 separates the pre-reaction treatment domain 102 and reaction domain 104; V3 and V 4 separate the reaction domain 104 from the post-reaction separation domain 106; V2 separates the reaction domain 104 from the storage reservoir 220; and V5 separates the reaction domain 104 from the addition reservoir 236.

In a preferred embodiment, the valves may also be used to pump fluid from the reaction domain 104 into the post-reaction separation domain 106. This pumping generally requires at least three diaphragm valves as disclosed in U.S. Patent Application Publication No. 2006/0073484 to Mathies et al., which is disclosed herein by reference. As shown in the valving system of FIG. 3, pumping is effected using the V3 and V4 in combination with V2 or V5. In this configuration, V2 or V5 are inlet valves for the pumping injection, V3 is the diaphragm valve, and V4 is the outlet valve. Pumping can be performed in a series of stages. In a first stage, the output valve is closed and an input valve is opened. In a second stage, a diaphragm valve is opened. In a third stage, the input valve is closed. In a fourth stage, the output valve is opened. In a fifth stage, the diaphragm valve is closed, pumping fluid through the open output valve.

Figure 4:
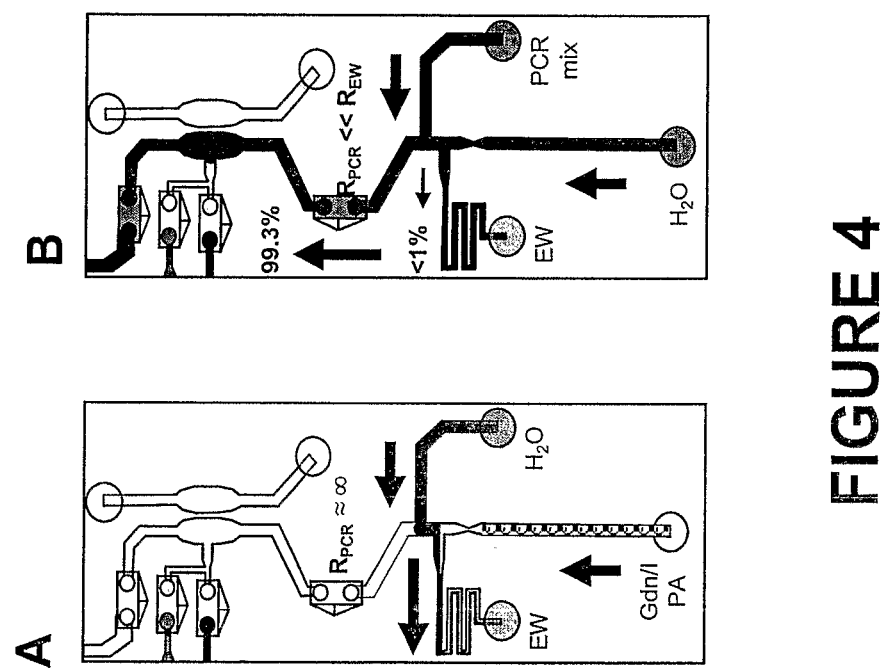
FIG. 4 are drawings showing flow pattern with V1 in a closed position (4A) and an open position (4B).

During operation of the system 100 of FIG. 2, an analyte from a sample is purified and concentrated in the pre-reaction treatment domain 102 prior to being introduced into reaction domain 104. FIG. 4 illustrates how differential channel flow resistances, valves, and laminar flow are used to isolate extraction solvents on the pre-reaction treatment domain 102 from the other domains. This operation usually involves two steps: 1) load and wash; and 2) elute. A sample (usually lysed cells) and its delivery fluid are sequentially delivered through the main channel 200 from the sample inlet 206, while at the same time a wash solution maintains flow through the side arm channel 202 from the extraction reservoir 208 (FIG. 4A). With valve $V_1$ closed during load and wash steps are pre-reaction treatment domain 102 and the reaction domain 104 are isolated and flow is directed toward its only available path, to the exit arm channel 204. With this design, problems arising from incompatibility of the fluids used in the pre-reaction treatment domain with the reaction or the valves are avoided, because the wash solution effectively serves as a barrier to sample solvents (usually organic solvents).

During the elution step (FIG. 4B), valves $V_1$ is opened to allow the purified analyte to be transferred to the reaction chamber 212. With $V_1$ open, flow is driven to the reaction domain as the high flow resistance exit arm channel 204 functions as a large fluidic resistor. Dominant flow, preferably >99%, to the reaction domain 104 is achieved by a combination of balanced flow resistance ratios and valving.

Figure 10:
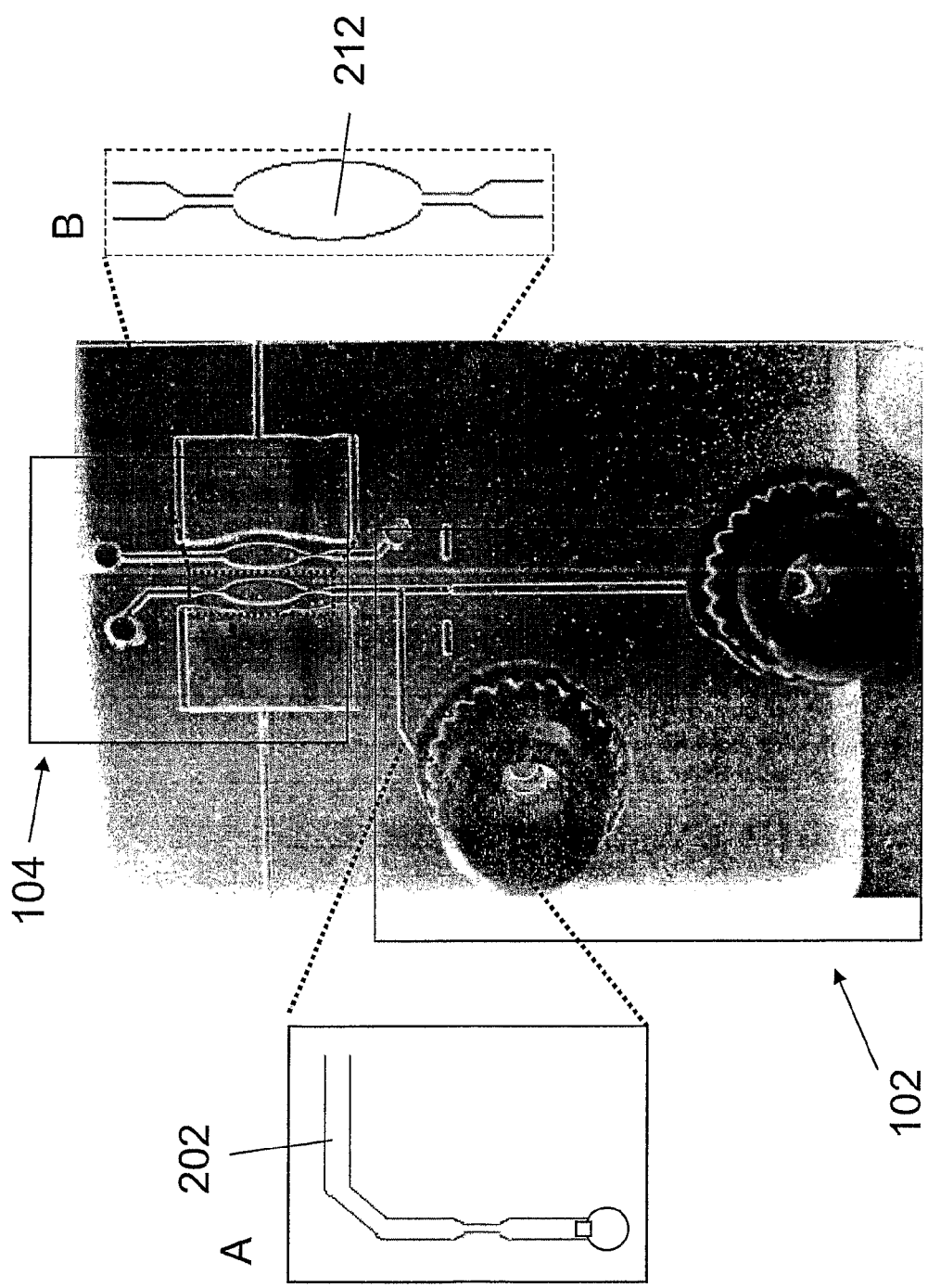
FIG. 10 shows an embodiment of the present invention where no valves are used between the pre-reaction treatment domain and the reaction domain. A) shows a blown-up view of the side arm channel. B) shows a blown-up view of the reaction chamber.

Although flow control between the pre-reaction treatment and reaction domains is preferably accomplished through valving, it may also be accomplished without valves. In this valveless embodiment, the treatment of the sample in the pre-reaction treatment domain is timed so that the optimal amount of purified reactant(s) arrives at the reaction chamber. This timing method is discussed in Legendre et al., *Anal. Chem.*, 2006, 78:1444-1451, which is incorporated herein by reference. As depicted in FIG. 10, if no valve is used, it is preferred that the side arm channel 202 contains a constriction therein, and that the reaction chamber contains a constriction immediate to its inlet and outlet. These constrictions are designed to resist fluid movement due to small pressure changes in the system. For example, when a syringe pump is removed from an inlet port, such as the sample inlet 206, a pressure change in the system results, which may cause the fluid in the system to move, such as the reactants moving out of the reaction chamber 212. The constriction provides a resistance to inhibit flow due to small pressure changes, such as that due to syringe removal.

In the case where the reaction is PCR and the analyte is nucleic acid, the sample usually includes lysed cells sample containing guanidine and isopropanol, which are not compatible with the PCR process. In addition, the column is preferably packed with silica to selectively purify the nucleic acids from the sample. The sample is loaded on to the silica to adsorb the nucleic acid. After loading and washing, the nucleic acid is then eluted from the silica, for example, at a different pH than the loading pH. The pre-reaction treatment can involve any nucleic acid purification nucleic acid extraction method known in the art including, but not limited to, those disclosed in WO 2006/093865; U.S. Pat. No. 6,914, 137; Nakagawa et al. (*J Biotechnol* 2005, 116:105-111); Christel et al. (*Journal of Biomechanical Engineering* 1999, 121:22-27); which are all incorporated herein by reference.

The reaction domain 104 receives the purified analyte from the pre-reaction treatment domain and subjects it to a reaction in the reaction chamber 212. The reaction may, but is not limited to, PCR, hybridization, antibody-antigen interaction, enzyme substrate interaction, or the like. In a preferred embodiment, the reaction is a PCR. This requires obtaining nucleic acids from the pre-reaction treatment domain 102 and performing thermal cycling. In addition to the purified nucleic acids, the reaction chamber may also accept nucleotides, polymerase, and other reactants from the extraction reservoir 208. The PCR mixture is brought together in the reaction chamber 212 and subjected thermal cycling. Heating localized to the reaction chamber 212 may be accomplished, for example, by using the methods disclosed in WO 2006/039293 to Easley et al., which is incorporated herein by reference. In other embodiments, the whole integrated chip may be placed into a thermocycler to effect nucleic acid amplification.

Once the reaction is complete, the content of the reaction chamber 212 is lead to the post-reaction separation domain 106. This is preferably accomplished by pumping action using the valves as describe above. For a PCR reaction, while the products are being pumped out of the reaction chamber 212, a molecular weigh standard maybe added to the reaction exit channel 216 via the addition reservoir 236. In certain embodiments, the addition reservoir 236 may also be used to dilute the reaction products prior to injecting them into the post-reaction separation domain 106.

The separation domain may perform various functions, including, but not limited to, electrophoresis, hybridization, isoelectric focusing, molecular filtration, molecular sieving, or chromatography. There post-reaction separation domain may contain an appropriate separation matrix such as a gel, other solution suitable for electrophoresis or isoelectric focusing, as is known in the art. Where the reaction is PCR, the separation is preferably a capillary. Capillary electrophoresis is well-known in the art and one skilled in the art should be able to apply those techniques to the present post-reaction separation domain. For the present invention, electrophoresis is preferably achieved by applying a potential difference between the buffer reservoir 234 and the waste reservoir 230. Various sieving matrices are also known in the art and all are appropriate for the present invention. The preferred electrophoresis method includes that disclosed by Easley et al. (*Lab Chip*, 2006, 6:601-610), which is incorporated herein by reference.

Although the preferred embodiments disclosed above include a pre-reaction treatment domain, a reaction domain, and a post-reaction separation domain, any one or more of these domains, by itself, can be used within the scope of the present invention. For example, in certain embodiments, the pre-reaction treatment domain may be used by itself. In other embodiments, the pre-reaction may be fluidly connected to a reaction domain without requiring a post-reaction separation domain.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

Example 1

Experimental Methods

Microchip Fabrication and Device Dimensions.

A microfluidic genetic analysis (MGE) device was made in accordance with FIGS. 2-4. The system had a microchannel architecture with three distinct functional domains—two for sample preparation (solid phase extraction (SPE), PCR) and one for electrophoretic analysis (ME). A total of five elastomeric, normally-closed valves (5) directed flow from a single syringe pump and localize the chemistries and reaction conditions that exist (FIG. 3).

All glass microchips were fabricated as previously described (Manz et al., *Trends Anal. Chem.*, 1991, 10:144-149, which is incorporated herein by reference) utilizing standard photolithography, wet etching, and thermal bonding (640° C., 6 h). Borofloat glass slides (127 mm×127 mm×0.7 mm) were purchased from Telic (Valencia, Calif., USA), pre-coated with chrome and positive photoresist (AZ1500 resist, 5300 Å). Differential etch depths (using a buffered HF solution) were achieved using HF-resistant dicing tape (Semiconductor Equipment Corporation, Moorpark, Calif., USA), patterned manually with a razor blade and removed at different times during the etch step to produce channels of varying depths. Dimensions of the device were as follows: Initial feature widths for the SPE domain were 25 µm. The SPE bed chamber (1 cm to weir) and side channel were etched to 200 µm deep (425 µm wide at top), with the waste channel 50 µm, and the weir 15-20 µm deep. The PCR domain was 200 µm deep, with the separation domain 50 µm in depth (125 µm wide at top). The separation domain was 5.3/3.0 cm total/effective length, with a starting mask width of 25 µm; an alignment channel was etched adjacent to the separation channel for laser adjustment. The ME sample exit arm was widened to 500 µm and the buffer arm to 300 µm. PCR and reference chambers were elliptical, with radii of 1.5 and 0.375 mm (typical reaction volume of 550 nL). Valve control lines had a starting width of 50 µm (125 µm final width), and all valve seats were rectangular (2.0 mm×0.5 mm, typical seat volume of 50 nL).

The four-layer integrated devices (30.0 mm×63.5 mm) were assembled as follows. The bottom two glass fluidic layers were fabricated as described, with access holes drilled into the patterned layer pre-bonding using "triple ripple" diamond tipped bits of 1.1-mm or 0.5-mm diameter (Abrasive Technology, Lewis Center, Ohio, USA). Following thermal bonding, glass was further removed from around the PCR chamber by etching with 49% HF, using HF-resistant tape as a mask. The third layer consisted of a commercially available PDMS membrane (HT-6240, Bisco Silicones, Rogers Corp., Carol Stream, Conn., USA), with a thickness of 254 µm, to be used as the deflectable valve layer. This unpatterned layer was irreversibly sealed via plasma oxidation (PDC-32G plasma cleaner, Harrick Scientific, Pleasantville, N.Y., USA) to a fourth glass layer patterned with the valve control channels and drilled using the techniques above. These third and fourth layers were aligned, then pressed to seal against the thermally-bonded glass microchip, with the third (PDMS) layer in contact with the drilled access holes of the second layer to form pneumatically-addressable valve seats in a normally-closed configuration.

Device Preparation.

Although the devices were designed for disposability, they were reused in this work for purposes of characterization. The glass microchips were cleaned prior to each experiment (before addition of the valve layer), to regenerate the surface (4). The PCR and ME domains were exposed to a 1:1 methanol:HCl solution for 30 minutes, rinsed with water, followed by exposure to concentrated $H_2SO_4$ for 30 minutes. The SPE domain was cleaned with 2 M HCl for a total of 1 hour. The entire device was then rinsed thoroughly with water and the PCR and SPE domains dried thoroughly with nitrogen. The SPE and PCR domains, along with the syringe used to deliver master mix, were silanized using Sigmacote (Sigma-Aldrich, St. Louis, Mo.). Following silanization, the SPE and PCR domains, as well as the syringe, were rinsed with water to remove acidic byproducts and dried thoroughly under nitrogen.

Macro-to-Micro Interfacing.

After conditioning, the device was loaded into a Plexiglas™ cartridge for interfacing. The cartridge consisted of two machined layers between which the device was sandwiched. Viton O-rings were used for fluidic and pneumatic seals; and the device was held in place using stainless steel knurled head screws. The cartridge was machined with access holes and fluidic reservoirs, interconnects for pneumatic control, and openings for IR heating and fluorescence excitation and emission. With the sample contained entirely in the device, the manifold afforded automation with ease of transfer between instrumentation specific to each domain.

Solid Phase Extraction.

For all extractions using the MGE system, silica beads (5-30 µm) were packed in the SPE domain against the etched weir using applied vacuum and replaced prior to each analysis to prevent carryover contamination. The bed was conditioned with 6M guanidine-HCl, pH 6.1, for 10 minutes prior to each analysis. The extraction protocol used for all experiments, adapted from Legendre et al. (*Anal. Chem.*, 2006, 78, 1444-51, which is incorporated herein by reference), consisted of three pressure-driven steps, each accomplished at a flow rate of 4.16 µL $min^{-1}$ using a Harvard Apparatus model 22 dual-syringe pump (Holliston, Mass.) and 250 µL Hamilton gastight syringes (Las Vegas, Nev.). Syringes were connected to the inlet reservoirs (sample inlet 206 and extraction reservoir 208) using NanoPort reservoirs and PEEK tubing (Upchurch Scientific, Oak Harbor, Wash.).

The extraction protocol for generating the real-time qPCR elution profile began with a sample consisting of 4 µL of human whole blood, lysed in a solution of 5 µL proteinase K and 91 µL of 6 M guanidine-HCL The resultant lysed sample was loaded onto the device for 6 minutes and washed with 80% isopropanol (80/20, v/v 2-propanol/dd $H_2O$) for 5 minutes for removal of proteins and cellular debris. Finally, water was passed through the bed and thirteen, 1.5 µL fractions of eluate were collected for subsequent qPCR amplification (n=2). The entire extraction was performed with secondary flow of dd$H_2O$ through the sidearm to imitate a fully-integrated analysis.

To generate the replicate breakthrough profiles (FIG. 5 inset), the same concentration of lysed blood sample as described above was used for consecutive breakthrough plots (n=3), with the silica bed removed and replaced between each run. Sample was flowed through the SPE bed as previously described (without secondary flow through SA), while 10, 1.5 µL fractions were collected at the SPE outlet. Subsequently, these fractions were fluorescently assayed for DNA concentration (7), using the Picogreen assay (Invitrogen™ Molecular Probes™, Eugene, Oreg.) according to the manufacturer's instructions.

For the integrated experiments, real clinical samples were used in order to show versatility of the device for handling multiple sample types and applications. The first sample evaluated was the detection of anthrax in mouse blood (Example 3). The C57BL/6 mice were injected with 1×10⁹ spores (*B. anthracis* strain 7702) in 100 μl water. Typically, mice challenged in this manner succumb 5-6 days post-challenge. All of the mice used in this experiment were positive for CFUs in the blood, liver, and spleen by day 2 post-challenge, and were asymptomatic when sampled on day 2.

The clinical patient sample was a discarded clinical sample from University of Virginia Medical Laboratories and all patient identification information was removed from the sample before it was obtained (Example 4). The sample consists of a nasopharyngeal wash that tested and diagnosed as a strong positive for *B. pertussis*. Samples were prepared by mixing the appropriate volume of sample (8 μL nasal aspirate or 6 μL murine whole blood) with 5 μL Proteinase K, diluted to 100 μL, total volume with 6 M GuHCl, and vortexed for 30 s to mix thoroughly. Following this treatment, human samples were used directly in the analysis, while mouse blood samples were first boiled for 10 minutes to aid release of DNA from the *B. anthracis* spores.

The sample was loaded for 3 minutes, followed by a 5 minute rinse with 80% isopropanol. A pre-elution rinse step was added to the extraction for full integration, in which no solution was flowed through the extraction bed and PCR master mix was flowed through $R_2$ and PCR domain with valves $V_1$ and $V_2$ open for 2 minutes to condition the PDMS valve connecting SPE and PCR. Elution of DNA from the solid phase was accomplished with water, with the valves remaining closed until the appropriate time as previously determined by qPCR, followed by subsequent opening and closing of the valves to allow PCR master mixture and eluting DNA to be trapped within the PCR chamber for thermal cycling.

PCR Amplification.

The real-time quantitative PCR (qPCR) experiments were performed using the iCycler (Bio-Rad, Hercules, Calif.). The qPCR experiments utilized amplification of the human thyroid peroxidase gene via Taqman® chemistry following the protocol developed by Horsman et al. (*J. Forns. Sci.* (in press)).

For fully integrated analysis, the PCR master mixture was made with the following final concentrations: 20 mM tris, 100 mM KCl pH 8.3, 6 mM $MgCl_2$, 0.8 μM of each primer, 0.4 mM dNTP, and 0.5 units/μL Taq polymerase. The thermal cycling protocols used were 95° C. for 30 seconds (initial denaturation), then 30 cycles of 95° C. for 2 seconds, 62° C./55° C. for 3 seconds (for *B. anthracfs* and *B. pertussis*, respectively), and 72° C. for 5 seconds, followed by a single final extension for 1 minute at 72° C. after the 30 cycles were completed. The primers for *B. pertussis* amplification (Example 3) were adapted from Loeffelholz et al. (*J. Clin. Microbiol.*, 1999, 37:2872-6, which is incorporated herein by reference). The primers used in the *B. anthracis* amplification (Example 4) were 5'-CAAATCAGCTCGAAAGTTAGGA (forward) (SEQ. ID. NO.: 1) and 5'-CAGTAACTGTTCAGAAGGTACATCTGA (reverse) (SEQ. ID. NO.: 2) for the amplification of a 211 bp fragment of the virulence B gene on pX01 and were designed in-house.

The non-contact thermal cycling PCR system was constructed in-house as previously described (Easley et al., *Anal. Chem.*, 2005, 77:1038-1045, which is incorporated herein by reference). Briefly, this system consisted of a laptop connected to a 50 W tungsten lamp (CXR/CXL, General Electric, Fairfield, Conn.) and cooling fan through a DAQ-6024 E-series card (National Instruments, Austin, Tex.). A miniature type-T copper-constantan thermocouple (model T-240C), obtained from Physitemp Instruments, Inc. (Clifton, N.J.), was inserted into the reference channel for temperature detection. A model TAC-386-T thermocouple-to-analog converter (Omega Engineering, Stamford, Conn., USA) powered by a 9-volt alkaline battery, amplified the thermocouple signal 25-fold. This signal was further amplified 75-fold using a difference amplifier circuit, and a RC low-pass filter ($f_o$=42 Hz) was included to remove 60 Hz line noise. The total 1875-fold amplified thermocouple signal (giving 75.0 mV/° C.) was then fed into a laptop computer containing a data acquisition card (6024-E, National Instruments, Austin, Tex.). A Lab VIEW application was written in-house to collect the thermocouple signal in order to control the tungsten IR heating lamp (CXR, 8 V, 50 W, General Electric, Cleveland, Ohio, USA) and the simple electronic cooling fan through solid state relays using a proportional-integral-derivative (PID) feedback control algorithm. The lamp and fan were powered by a 5V/12V power supply (HCBB-75W-A, Power-One, Camarillo, Calif., USA), and the amplification circuitry was powered by 9V batteries. A foil mirror positioned above the microchip promoted efficient heating during PCR.

Valving Instrumentation.

An oil-less diaphragm vacuum pump/compressor (Gast Manufacturing, Inc., Carlstadt, N.J., USA) was used to control the pneumatic valve lines by application of pressure (15 kPa) to keep valves closed or vacuum (60 kPa) to open them. Actuation of these valves was accomplished using 12 V solenoid valves and corresponding manifold (Parker Pneumatic, Richland, Mich., USA). A valve controller was built in-house using quad high side drivers as digital switches to route the 12 V power source to the solenoid valves, and was controlled using an in-house written Lab VIEW application. The controller was also equipped with manual switches.

On-Chip Pressure Injection.

The injection protocols were carried out as described previously (Karlinsey et al., *Anal. Chem.*, 2005, 77:3637-43; and Easley et al., *Lab Chip*, 2006, 6, (in press); which are incorporated herein by reference). The chip design made it possible for a direct injection from the PCR chamber or marker reservoir, a laminar injection from both, or a biased laminar injection from both. Actuation times, controlled by an in-house written Lab VIEW application, were as follows: 20, 50, 20, 20, 20, 20 milliseconds (ms) for direct or laminar injections (total of 150 ms); 20, 20, 20, 50, 20, 20, 20, 20 ms for biased laminar (total of 190 ms). A 250 ms delay was also typically included between injection and applied voltage to minimize distortion of peak shape from pullback effects typical to diaphragm pumping.

Microchip Electrophoresis.

Glass microchips were cleaned as previously described. The separation channels were not allowed to dry after this cleaning procedure. During PCR, the separation domain was filled with 1.0 M $HNO_3$. Following PCR, the separation channels were rinsed with distilled water and filled with the sieving matrix, 3.5% HPC in 80/40 mM MES/Tris (15) with 1.0 YOPRO DNA intercalating dye (Invitrogen™ Molecular Probes™). Following pressure injection, separation was achieved by applying voltage using a dual polarity high-voltage power supply built in-house using two Spellman high-voltage sources (Hauppauge, N.Y., USA). For *Bacillus anthracis* analysis, −200 V was applied to the buffer reservoir and 1050 V to the buffer waste. For the *Bordetella pertussis* analysis, −150 and 790 V were applied. An argon ion laser (Model LS200, Dynamic Laser, Salt Lake City, Utah, USA) was used for excitation with a conventional confocal detection setup (16× objective, 1-mm pinhole). Emission was collected with a PMT (Hamamatsu, Bridgewater, Conn., USA) through a 515-nm bandpass filter (Omega Optical, Brattleboro, N.Y., USA). The instrument and data acquisition were controlled through a Lab VIEW application.

Conventional Analysis.

Conventional sample processing of nucleic acid extraction, DNA amplification, and separation and detection is routinely performed in the lab before transferring the technique to the microchip format. For SPE, a MinElute Spin Column was used (Qiagen, Valencia, Calif.). Following the manufacturer's protocol, this step requires 1.8 mL in wash and elution solutions, with the process requiring ~20 mins. For PCR, a conventional thermal cycler was used (Bio-Rad, Hercules, Calif.), with a 25 µL solution for the amplification reaction. With a conventional amplification protocol to match the conditions listed in the PCR Amplification section, the duration of the amplification was 90 mins, significantly increased due to the increased heating and cooling rates. For the ME step, the amplification products were injected into a 50 □m I.D. bare silica capillary with an electrokinetic injection and separated under the same conditions described previously using an MDQ capillary electrophoresis instrument (Beckman-Coulter, Fullerton, Calif.). The separation was completed in 10 minutes.

Example 2

Flow Control

Figure 5:
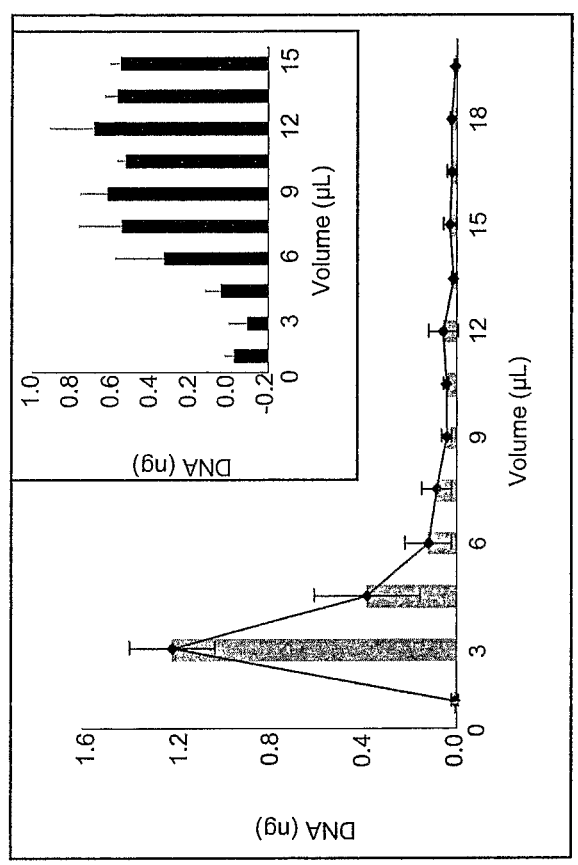
FIG. 5 is a graph showing the elution profile of a human genomic DNA extraction from blood using real-time qPCR to determine the amount of DNA eluted from the MGA device. The results demonstrate which volume fractions will be most appropriate for use in downstream PCR amplification in the fully-integrated analysis. Replicate breakthrough profiles were also obtained (inset), and the capacity of the solid phase was determined to be 3.3 ng DNA.
Figure 6:
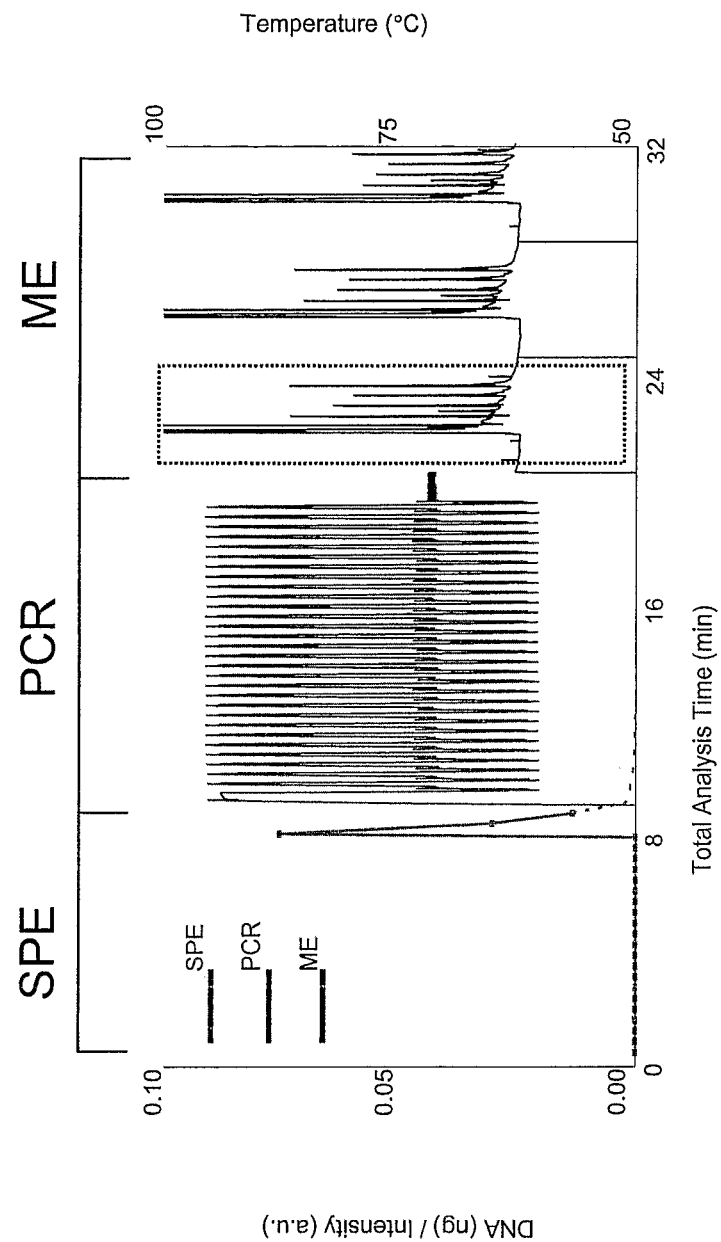
FIG. 6 is a graph showing the detector response during all three stages of sample processing during the integrated detection of *Bacillus anthracis* from murine blood. Detector responses during all three stages of sample processing and analysis are portrayed in terms of total analysis time. The SPE trace (green) was taken from an offline DNA extraction of the same murine sample and is representative of the total DNA concentration observed in a typical extraction. The temperature (blue) and fluorescence intensity (black) represent online data, with a total analysis time of less than 24 minutes. Three sequential injections and separations were carried out to insure the presence of amplified product.
Figure 7:
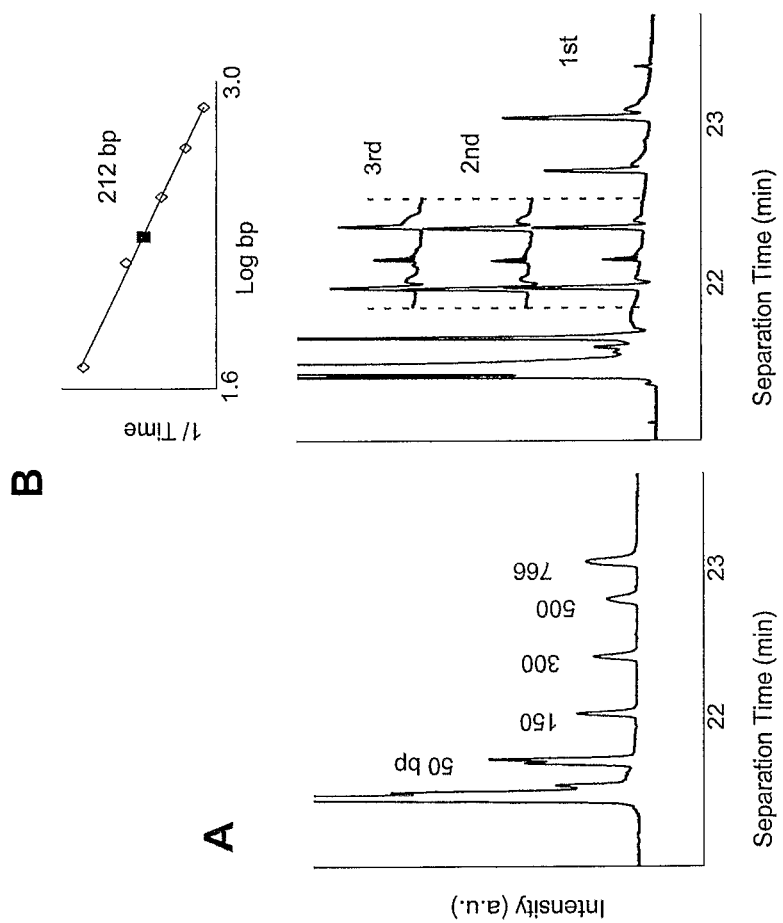
FIG. 7 are graphs showing further results of *Bacillus anthracis* detection: (A) fluorescence data from an integrated analysis of a blank sample (no DNA loaded) control with marker peaks labeled; and (B) a zoomed in view of the first separation shown in FIG. 6, with the product peak marked and sized. The second and third runs are overlaid with the time axis cropped. The inset plot shows the sizing curve of inverse migration time vs. log(base pairs) with both the sizing standard peaks (open diamonds) and product (square) plotted for all 3 runs shown in FIG. 6 (error bars included). From this data, the product was sized as 212±3 bp.

The MGA device was tested to ensure contamination-free integration of SPE and PCR. Since the SPE process is not monitored on-line, chromatographic timing was established off-line. Fractions (1.5 µL) were collected from the SPE bed outlet during extraction and evaluated for nucleic acids by fluorescence or for PCR-amplifiable DNA by quantitative PCR (qPCR). A fluorescence assay was used to determine the timing needed for valve $V_1$ opening to allow eluted nucleic acids to be transferred to the PCR chamber, however, qPCR revealed that the fractions with the largest mass of DNA did not contain the most PCR-amplifiable DNA. This trend was likely the result of PCR inhibition due to residual isopropanol contamination. FIG. 5 detailed the qPCR analysis with replicate DNA extractions from human whole blood. The majority of DNA was eluted in 2-5 µL; and fraction 2 consistently provided the most PCR-amplifiable DNA, thereby defining the timing for valve $V_f$. SPE capacity was determined by flowing human genomic DNA through the bed and measuring the breakthrough volume (FIG. 5, inset), revealing a capacity of 3.3 ng for a whole blood lysate, a mass sufficient for downstream DNA amplification. After completion of SPE, flow control for the remainder of the analysis was maintained using elastomeric valving/pumping. The valves were used to isolate the purified DNA in the PCR domain during amplification, then to pump from the PCR domain to the ME domain for injection and analysis.

Example 3

Detection of *Bacillus antltracis*

In order for a µ-TAS to have value in clinical diagnostics or forensic genetic profiling, it must be capable of accepting whole blood and generating a genetic profile, a difficult task due to the multiple PCR inhibitors associated with this starting sample. The utility of the MGA device was evaluated with blood drawn from C57BL/6 mice injected intraperitoneally with *Bacillus anthracis* spores, prior to onset of symptoms. All blood samples were positive for *B. anthracis* colony-forming units, and all mice subsequently succumbed to infection. The blood was mixed with lysis buffer, and a volume equivalent to 750 nL of whole blood was loaded for integrated analysis (FIG. 6). The extraction was completed in less than 10 minutes and, upon capture of the purified DNA in the 550 nL PCR microchamber, amplification was invoked using infrared (IR) thermal cycling. Subsequently, a 211 base-pair fragment found on plasmid pX01 of *B. anthracis* was amplified in 11 minutes.

Post-amplification, the product was pressure-injected into the separation domain, with a DNA sizing standard for electrophoretic evaluation (FIG. 7A). Three valves ($V_2$, $V_3$, and $V_4$) provided a diaphragm pumping system (as describe earlier) with the capability to directly inject amplicon, while $V_5$ could be actuated simultaneously with $V_2$ to perform a co-injection of DNA marker. This method allowed for control of the relative volumes injected into the separation channel from two or more sources. In addition, the flow resistances in the separation domain were designed to direct the majority of the flow across the main separation channel 224 and into buffer waste reservoir 230 (FIG. 2), minimizing the plug width for separation.

Following injection of amplified material, electrophoretic separation was performed under high fields with laser-induced fluorescence (LIF) detection. With injection, separation and detection completed in less than 180 seconds, total analytical time for the entire analysis (extraction, amplification, separation and detection) was less than 24 minutes (FIG. 6), an order of magnitude reduction in time relative to analysis using conventional methods. The ability to simultaneously inject DNA standard with amplified material from the PCR chamber provided a simple mechanism for determining both the presence (blank profile in FIG. 7A, 'positive' in FIG. 7B) and size (FIG. 7B inset) of the amplicon. The presence of anthrax in the sample was confirmed by the 211-bp product corresponding to the targeted sequence found on plasmid pX01 of *B. anthracis*. Moreover, with only a few tens of nanoliters injected from the 550 mL PCR chamber, copious amounts of amplified material remained for replicate analysis. Multiple injection/separation cycles could be carried out post-PCR for confirmation of the identity of the product peak, at a cost of only a few hundred seconds (FIG. 7B). When eight co-injections of amplicon with DNA standard were carried out, the resultant size was determined to be 211±2 bp using the local Southern sizing method (Elder, J. K. & Southern, E. M., *Anal. Biochem.,* 1983, 128, 227-231). These results represent the first instance in which an integrated microfluidic device was utilized for all processing and analysis steps in the direct analysis of a blood sample to genetically verify the presence of a pathogen in under 25 minutes. Since the early detection of anthrax is critical to the survival of the host by early recognition and administration of antibiotics with post-exposure vaccination, the MGA system and its integrated methods provide a microfluidic path to improving biodefense surveillance measures.

Example 4

Detection of *Bordetella pertussis*

To demonstrate the broader utility of the MGA system, a different sample and nucleic acid target was evaluated. A nasal aspirate was obtained from a human patient symptomatic of whooping cough, a respiratory infection caused by the gram-negative bacterium *Bordetella pertussis*, which can be isolated from the mouth, nose, and throat. This infection is characterized by severe spasms of coughing that can last several weeks or months and, while not particularly threatening to those beyond their first year, it can lead to serious complications or fatality in infants (Hewlett, E. L. & Edwards, K. M., *N. Engl. J. Med.*, 2005, 352:1215-22; and Mattoo, S. & Cherry, J. D., *Clin. Microbial. Rev.*, 2005, 18:326-82).

Figure 8:
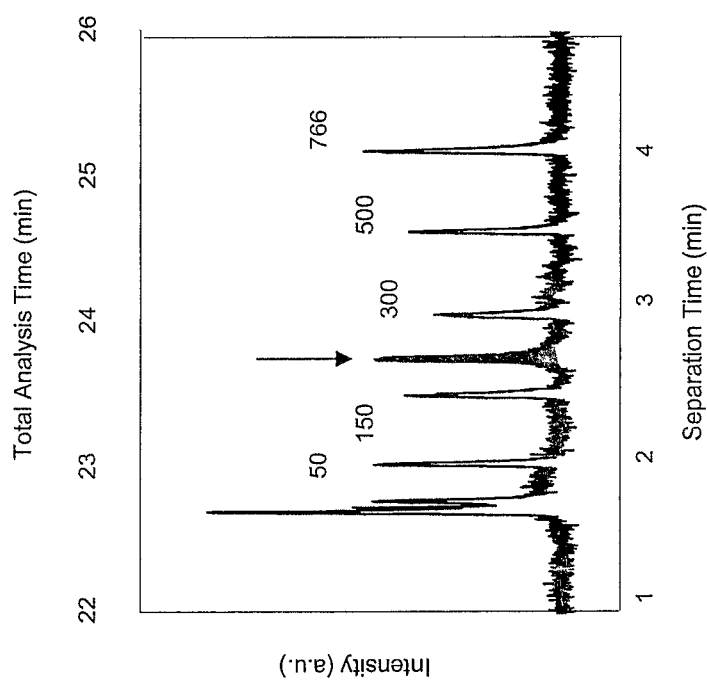
FIG. 8 is a graph showing the ME trace plotted alone from the *Bordetella pertussis* detection experiment. The ME trace plotted alone shows the separation of the co-injected DNA sizing standard (peak sizes labeled in number of base pairs) with the PCR amplicon for product verification. The amplicon (beneath arrow) migrates between the expected size standards, and sequencing analysis was used to further verify the product.

Using the same method described above, a volume equivalent to 1 µL of nasal aspirate was prepared in lysis buffer and loaded into the MGA device, with DNA purification carried out as described earlier. The presence of *B. pertussis* can be confirmed by an amplification of a 181-bp fragment of the IS481 repeated insertion sequence, and following PCR amplification of this target, the amplicon was injected into the separation channel for electrophoretic separation (FIG. 8). Again, co-injection of a DNA sizing standard was used to aid in the sizing of amplified product for comparison with the expected 181-bp fragment, confirmed by off-chip sequencing of the resultant amplicon. With a total analysis time of 24 minutes, the MGA system could provide physicians with a method to rapidly screen for *B. pertussis* respiratory infection in patients during early infection/exposure or for screening during outbreaks. This technological advance is timely as >25,000 *B. pertussis* cases were reported in 2004, a twelve-fold increase since 1980 (Hewlett, E. L. & Edwards, K. M., *N Engl. J. Med.*, 2005, 352:1215-22). The rapid turn-around time not only provides a dramatic improvement over conventional culturing methods for diagnosis (requiring a minimum of 24-48 hours (Mattoo, S. & Cherry, J. D., *Clin. Microbial. Rev.*, 2005, 18:326-82)), but also presents the possibility of point-of-care testing, a rapidly growing concept applicable to clinical diagnostics, forensics, environmental testing, food safety testing, and biothreat sensing in the field for armed forces.

Example 5

Comparison of MGA to Existing Systems

Figure 9:
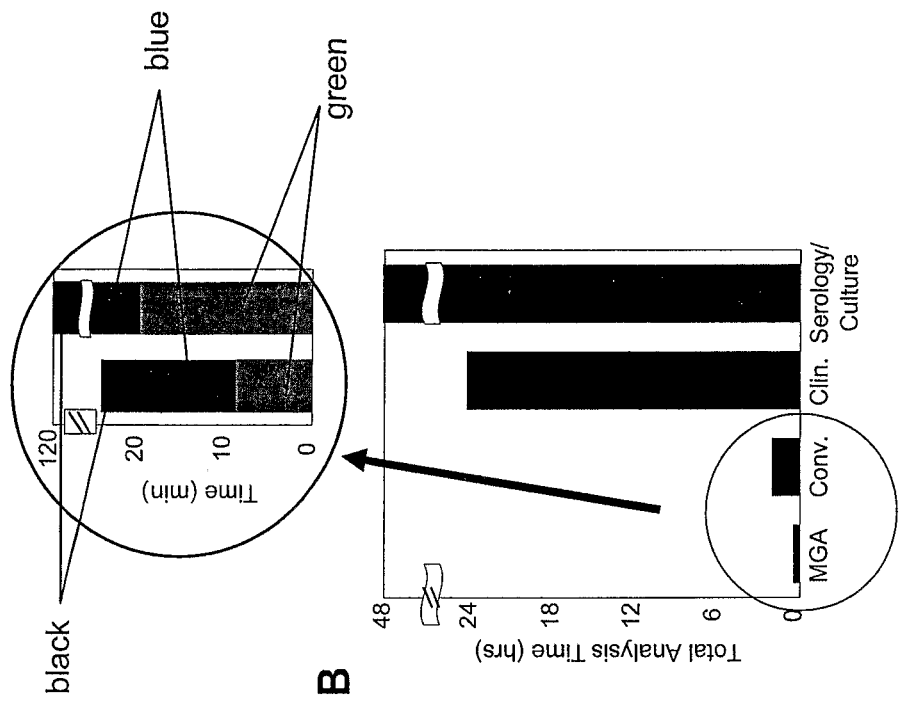
FIG. 9 are graphs showing further results of *Bordetella pertussis* detection: (A) (B) Volumes for SPE and PCR are compared for MGA and Conv., showing a significant reduction for both processes; (C) Analysis times for MGA and other systems are shown (the inset, with SPE (green), PCR (blue), and ME (black), shows the analysis times for each domain).
Figure 9:
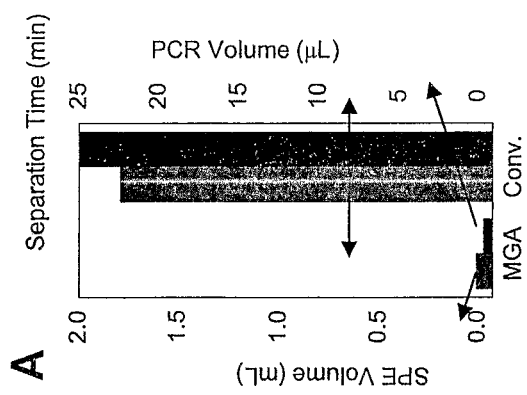

The advantages of the MGA system are obvious: rapid turn-around time, decreased reagent consumption per test, decreased operator variability (human error factor), and improved operator safety. The comparisons in FIGS. 9A and 9B showcase the capabilities of a MGA system with respect to reduction of analysis time. FIG. 9A compares the turn-around time of the MGA system for detecting *B. pertussis* from a sample, relative to conventional molecular-, serologic- and culture-based methods. The 24 minutes turn-around time compares favorably with >2 hours for analysis using conventional methods, a minimum of 24 hrs for PCR-based analysis in a clinical microbiological testing lab, and >48 hrs for serology and/or culturing of the organism. The inset highlights the comparison of the MGA system with conventional methods for extraction (green), amplification (blue), and detection (black) assuming standard laboratory instrumentation used by the same operators, with no lost time between processes, and does not take into account 'batching-related' delays. While not insignificant, the five-fold reduction in analysis time is out-weighed by the potential for automation of the integrated analysis, which will further decrease technician labor time and isolate the operator from the analysis. Finally, FIG. 9B highlights the value of a microfluidic system with respect to reduced consumption of reagents for DNA extraction and amplification. Microfluidic devices are expected to inherently scale reduction to the analytical system; and the MGA system allows for sub-microliter PCR. This not only enhances amplification speed, but also provides a 50-fold reduction in PCR volume. Consuming less Taq polymerase, the most costly reagent in this molecular analysis, yields the potential to dramatically decrease the cost per test. Concordantly, the ~25-fold reduction in volume of reagents used for DNA extraction reduces the hazardous waste that must be disposed of. The micro fluidic nature of the MGA system distinguishes it from larger volume, commercial systems that do not reap the benefits of sub-microliter fluid manipulation.

While the MGA device shares similarities with other microfluidic devices, it is important to define the distinguishing characteristics of this system. First and foremost, in contrast with other systems, the incorporation of a purification step with downstream analytical processing allows for the removal of inhibiting chemical compounds, enabling the input of complex biological samples such as blood, a key requirement of a genetic µ-TAS. This MGA system displays the first integration of DNA extraction from whole blood with multiple downstream processes (PCR and electrophoretic analysis) on the same microdevice. The second distinction is the simplistic design of this glass MGA device, which avoids costly and time-consuming metallization steps. Circumventing the need to fabricate heaters and/or temperature sensors into the PCR system enhances cost-effectiveness so that single-use disposability becomes a realistic possibility.

The addition of DNA purification for the removal of interfering species to already established microfluidic technology for PCR amplification, separation, and detection, completes the genetic analysis system and allows relevant genetic profiling for a variety of applications. Through the integration of sample pretreatment with analytical processing for the analysis of biological samples presented here, the goal of the µ-TAS has been realized. In an era witnessing a shift towards point-of-care testing and personalized medicine, the MGA system presents the first true microfluidic system capable of sample in-answer-out genetic testing. Its virtues are simplicity in function and fabrication, combined with the possibility for turn-key microfluidic detection systems for screening a panel of pathogens. With whole blood and nasal aspirate analyses demonstrated, it is clear that a variety of representative candidate samples-including body fluids (urine, blood, semen, etc), nasal swabs and fecal matter-could be analyzed in a microfluidic system designed for use in emergency rooms, primary care clinics, and forensic labs. An analytical platform that utilizes disposable, cost-effective microfluidic chips, reduces reagent consumption by orders of magnitude, and provides turn-around times of 30 min or less, offers the potential of rapid, inexpensive on-site screening. It is reasonable to expect that compact, portable instrumentation can be assembled around the small, disposable microfluidic device described here, to generate a portable and eventually, hand-held system, applicable in a number of clinical, biohazardous, and forensic contexts.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A microfluidic analysis system comprising:
an integrated microfluidic analysis assembly comprising:
a pre-reaction treatment domain located upstream from a downstream reaction domain, the pre-reaction treatment domain comprising:
a main channel;
a side arm channel connected to the main channel at a first point; and
an exit arm channel connected to the main channel at a second point located upstream from the side arm channel with respect to the downstream reaction domain;
a first valve; and
the reaction domain, fluidly connected to the pre-reaction treatment domain through the first valve;
wherein the exit arm channel has a higher flow resistance than the respective flow resistances of the main channel and the side arm channel; and
wherein the exit arm channel and the side arm channel are located to inhibit a solvent, flowing from the side arm channel to the exit arm channel, from contacting the first valve when the first valve is closed.

2. The system of claim 1, wherein the exit arm channel has a flow resistance at least 2 times greater than that of the main channel.

3. The system of claim 1, wherein the main channel contains an extraction media therein.

4. The system of claim 3, wherein the extraction media is silica.

5. The system of claim 1, wherein the reaction domain comprises a PCR chamber.

6. The system of claim 1, further comprising a storage reservoir; wherein the reaction domain fluidly connects to the storage reservoir.

7. The system of claim 6, wherein the reaction domain is separated from the storage reservoir by a second valve.

8. The system of claim 1, wherein the reaction domain fluidly connects to an addition reservoir.

9. The system of claim 8, wherein the reaction domain is separated from the addition reservoir by an additional valve.

10. The system of claim 1, wherein the integrated microfluidic analysis assembly includes a post-reaction separation domain fluidly connected to the reaction domain.

11. The system of claim 10, wherein the post-reaction separation domain contains a capillary electrophoresis channel.

12. The system of claim 10, wherein the reaction domain is separated from the post-reaction separation domain by a pair of valves arranged in series.

13. A method for making the microfluidic analysis system of claim 1 comprising:
providing an integrated microfluidic analysis assembly, including:
providing a pre-reaction treatment domain located upstream from a downstream reaction domain, the pre-reaction treatment domain comprising:
a main channel;
a side arm channel connected to the main channel at a first point; and
an exit arm channel connected to the main channel at a second point located upstream from the side arm channel with respect to the downstream reaction domain;
providing a first valve; and
providing the reaction domain, fluidly connected to the pre-reaction treatment domain through the first valve;
wherein the exit arm channel has a higher flow resistance than the respective flow resistances of the main channel and the side arm channel; and
wherein the exit arm channel and the side arm channel are located to inhibit a solvent, flowing from the side arm channel to the exit arm channel, from contacting the first valve when the first valve is closed.

14. The method of claim 13, wherein the exit arm channel has a flow resistance at least 2 times greater than that of the main channel.

15. The method of claim 13, wherein the main channel contains an extraction media therein.

16. The method of claim 15, wherein the extraction media is silica.

17. The method of claim 13, wherein the reaction domain comprises a PCR chamber.

18. The method of claim 13, wherein providing an integrated microfluidic analysis assembly includes providing a storage reservoir; and
wherein the reaction domain fluidly connects to the storage reservoir.

19. The method of claim 13, wherein providing an integrated microfluidic analysis assembly includes providing a second valve;
    wherein the reaction domain is separated from the storage reservoir by the second valve.

20. The method of claim 13, wherein providing an integrated microfluidic analysis assembly includes providing an addition reservoir;
    wherein the reaction domain fluidly connects to the addition reservoir.

21. The method of claim 20, wherein providing an integrated microfluidic analysis assembly includes providing an additional valve, the reaction domain is separated from the addition reservoir by the additional valve.

22. The method of claim 13, wherein providing an integrated microfluidic analysis assembly includes: providing a post-reaction separation domain fluidly connected to the reaction domain.

23. The method of claim 22, wherein the post-reaction separation domain contains a capillary electrophoresis channel.

24. The method of claim 22, wherein providing an integrated microfluidic analysis assembly includes providing a pair of valves arranged in series, the reaction domain separated from the post-reaction separation domain by the pair of valves arranged in series.

* * * * *